(12) United States Patent
Ward et al.

(10) Patent No.: US 7,862,519 B1
(45) Date of Patent: Jan. 4, 2011

(54) EASY-TO-USE MULTI-USE BODY FLUID SPECIMEN COLLECTION AND ANALYTE SENSING ASSEMBLY

(75) Inventors: W. Kenneth Ward, Portland, OR (US); Richard G. Sass, Portland, OR (US)

(73) Assignee: Isense Corporation, Wilsonville, OR (US)

( * ) Notice: Subject to any disclaimer, the term of this patent is extended or adjusted under 35 U.S.C. 154(b) by 1647 days.

(21) Appl. No.: 10/463,848

(22) Filed: Jun. 16, 2003

Related U.S. Application Data

(60) Provisional application No. 60/473,013, filed on May 21, 2003, provisional application No. 60/473,014, filed on May 21, 2003.

(51) Int. Cl.
*A61B 5/00* (2006.01)

(52) U.S. Cl. .................................................... 600/583

(58) Field of Classification Search ............... 600/583, 600/584, 573, 576, 578, 181, 575, 345, 347, 600/182, 365, 316, 547
See application file for complete search history.

(56) References Cited

U.S. PATENT DOCUMENTS

| | | | | |
|---|---|---|---|---|
| 4,953,552 | A | 9/1990 | DeMarzo | 128/635 |
| 5,165,407 | A | 11/1992 | Wilson et al. | 128/635 |
| 5,428,123 | A | 6/1995 | Ward et al. | 528/28 |
| 5,510,266 | A | 4/1996 | Bonner et al. | 436/43 |
| 5,660,163 | A | 8/1997 | Schulman et al. | 126/635 |
| 5,820,622 | A * | 10/1998 | Gross et al. | 604/890.1 |
| 5,871,494 | A | 2/1999 | Simons et al. | 606/181 |
| 6,051,392 | A | 4/2000 | Ikeda et al. | 435/25 |
| 6,228,100 | B1 * | 5/2001 | Schraga | 606/183 |
| 6,309,351 | B1 | 10/2001 | Kurnik et al. | 600/309 |
| 6,329,161 | B1 * | 12/2001 | Heller et al. | 435/14 |
| 6,352,514 | B1 | 3/2002 | Douglas et al. | 600/583 |
| 6,391,643 | B1 * | 5/2002 | Chen et al. | 436/14 |
| 6,477,395 | B2 | 11/2002 | Schulman et al. | 600/345 |
| 6,484,046 | B1 | 11/2002 | Say et al. | 600/345 |
| 6,534,017 | B1 | 3/2003 | Bottwein et al. | 422/104 |
| 6,592,745 | B1 | 7/2003 | Feldman et al. | 205/777.5 |

(Continued)

FOREIGN PATENT DOCUMENTS

| | | |
|---|---|---|
| WO | WO 01/73124 A2 | 4/2001 |
| WO | WO 01/64105 A1 | 7/2001 |

*Primary Examiner*—Max Hindenburg
*Assistant Examiner*—Fangemonique Smith
(74) *Attorney, Agent, or Firm*—Schwabe, Williamson & Wyatt, P.C.

(57) ABSTRACT

A multiple use analyte sensing assembly that includes a long, thin conductor. A plurality of sensing sites are spaced along the conductor and each sensing site includes a membrane system adapted to create a current when placed into contact with body fluid containing the analyte. The assembly also includes a housing, having an aperture, an uptake spool and a payout spool, the conductor being wrapped about the payout spool before the sensing assembly is used. A sensor positioning actuator turns the uptake spool to move each sensing site, in sequence, to the housing aperture and then to the uptake spool. The assembly also includes a skin broaching assembly, having a multiplicity of lancets and a lancet positioning actuator adapted to move each lancet to the aperture. In addition, a lancet use actuator is adapted to move each lancet at least partially through the aperture and then back again.

33 Claims, 3 Drawing Sheets

U.S. PATENT DOCUMENTS 6,988,996 B2 * 1/2006 Roe et al. .................. 600/584
2002/0169394 A1 * 11/2002 Eppstein et al. ............. 600/573
2003/0032892 A1 * 2/2003 Erlach et al. ................ 600/547
2004/0064068 A1 * 4/2004 DeNuzzio et al. ........... 600/583

* cited by examiner

EASY-TO-USE MULTI-USE BODY FLUID SPECIMEN COLLECTION AND ANALYTE SENSING ASSEMBLY

RELATED APPLICATIONS

This application claims priority from provisional applications Ser. No. 60/471,013 and 60/473,014, both of which were filed on May 21, 2003 and both of which are incorporated by reference as if fully set forth herein.

BACKGROUND OF THE INVENTION

Currently available multiple use glucose sensing assemblies rely on a multiplicity of individual sensing elements, currently in the form of strips of coated paper, each one bearing electrical contacts. As multiple use glucose sensing assemblies become more common, the issue of the expense of the individual sensing elements used in these assemblies becomes an increasingly important issue. Currently available sensing assemblies that contain an array of single use sensors typically cost on the order of $0.80 per measurement. Over the years this expense can increment to a considerable sum. A serious health concern arises from this expense because a diabetic patient might refrain from taking a blood glucose measurement that he would otherwise take, due to the expense of taking the measurement. In some instances the failure to take a blood glucose measurement could be fatal. Moreover, the more measurements a diabetic patient takes, the better understanding she will gain of the relationship between her insulin injection schedule; her food intake, stress and exercise levels; and her blood glucose level.

A number of impediments, however, stand in the way of arriving at a truly economical multi-use sensing assembly. Assemblies that use chemical coated paper strips must be refilled with these strips.

Another type of assembly (a "coated wire assembly") uses a wire having an electrochemically active metal (typically platinum) that is largely coated with insulation. A portion of this insulation is removed to form an electrode that is then covered with a assembly of membranes that produces an electric current when the analyte of interest (typically glucose) is present. In the production of a coated wire assembly it has been found that a problem is created in the removal of the wire insulation. With respect to insulated wires it has been found that the insulation is generally not applied in a truly concentric manner. Accordingly, if a laser beam is used to remove the insulation it tends to pit and stipple the electrochemically active surface of the wire, increasing its surface area. Although a large surface area is typically desirable, the process is unpredictable because of the unevenness of the insulation coat. As a result a non-uniformity is introduced into each set of sensing elements.

For a multiple use sensing assembly, because there is no calibration procedure, differing sensitivities at the various sensing sites result in a lack of repeatability in the formation of measurement and resultant inaccuracies.

Accordingly, a method of making a multiple use analyte sensing assembly that does not rely on chemical strips is desirable.

SUMMARY

The present invention is a multiple use analyte sensing assembly that includes a long, thin conductor. A plurality of sensing sites are spaced along the conductor and each sensing site includes a membrane system adapted to create a current when placed into contact with body fluid containing the analyte. The assembly also includes a housing, having a housing aperture and an uptake spool and a payout spool, located within the housing, the sensing sites being wrapped about the payout spool before the sensing assembly is used. Also included is a sensor positioning actuator for turning the uptake spool so that each sensing site is moved, in sequence, to the housing aperture and then to the uptake spool. The assembly also includes a skin broaching assembly, having a multiple lancet holding mechanism, a multiplicity of lancets held by the multiple lancet holding mechanism and a lancet positioning actuator adapted to move, in sequence, each lancet to a position coincident to the aperture. In addition, a lancet use actuator is adapted to move a lancet that is positioned coincident to the aperture, at least partially through the aperture and then back again.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENT

Figure 1:
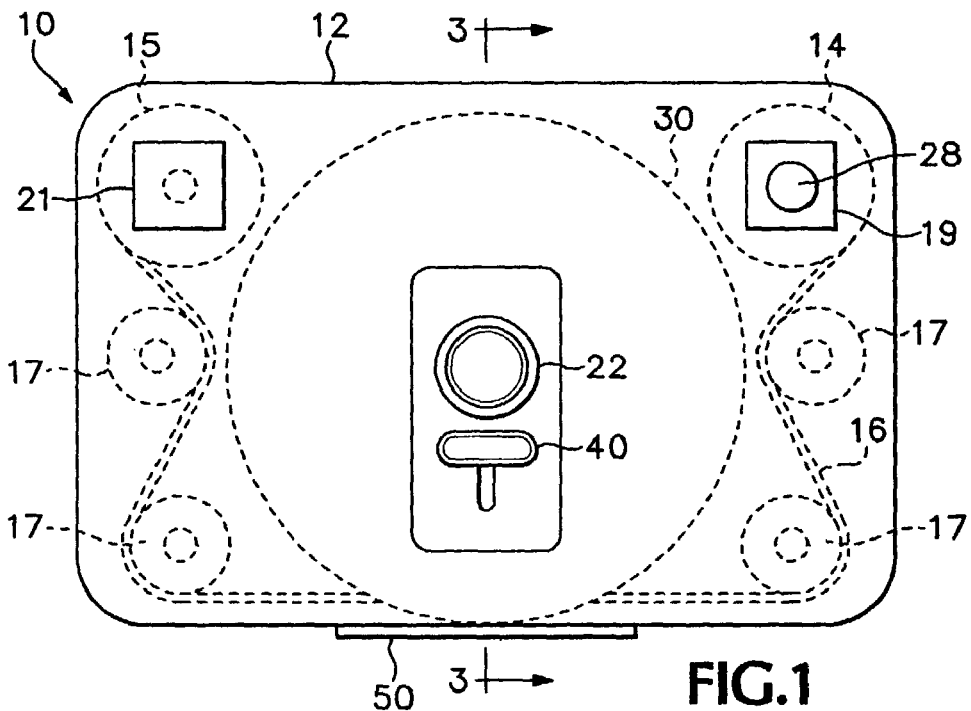
FIG. 1 is a side view of a cassette style multiple use analyte sensing assembly according to the present invention.
Figure 2:
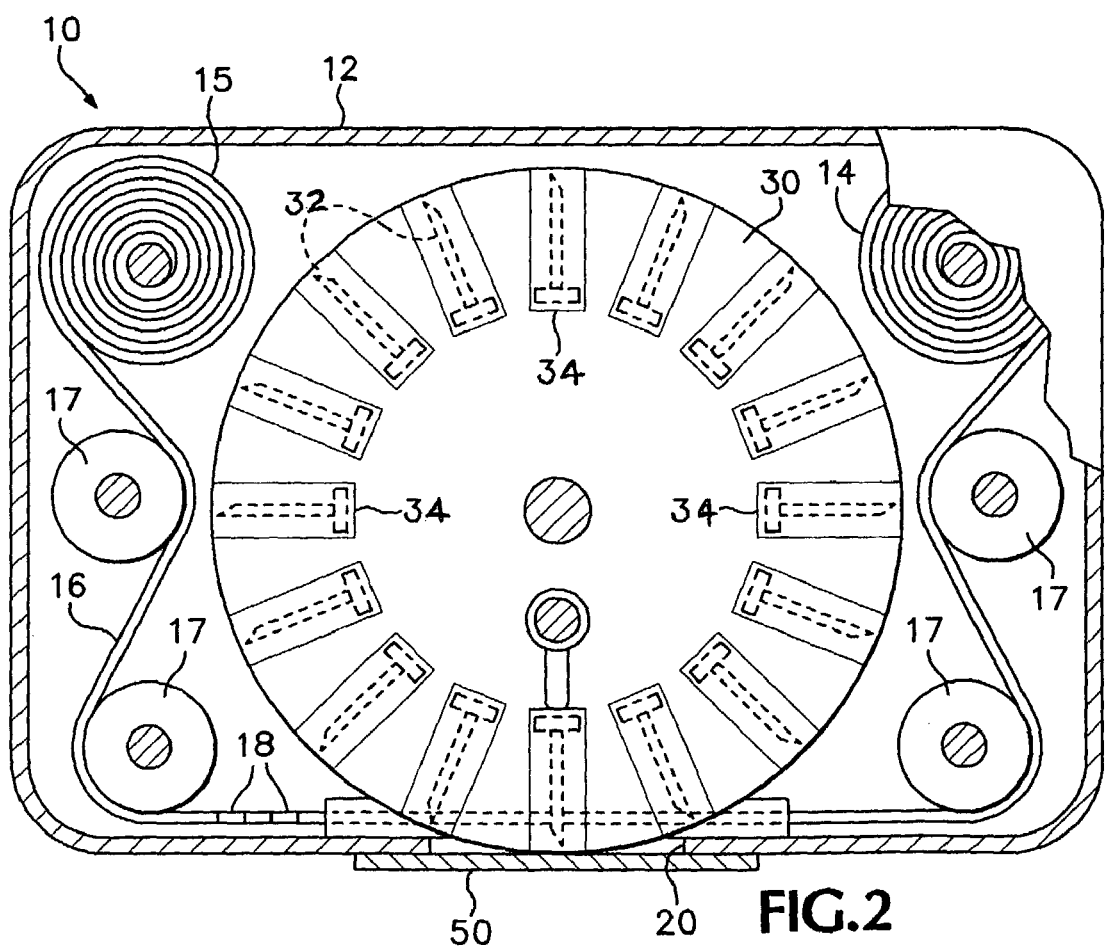
FIG. 2 is a side sectional view of the cassette style multiple use analyte sensing assembly of FIG. 1.
Figure 4:
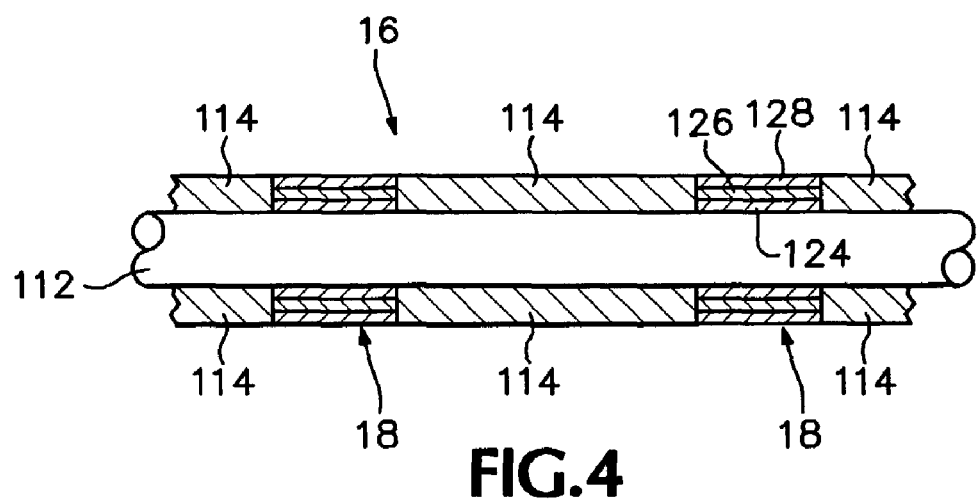
FIG. 4 is a greatly enlarged side view of the sense wire that is part of the present invention.
Figure 5:
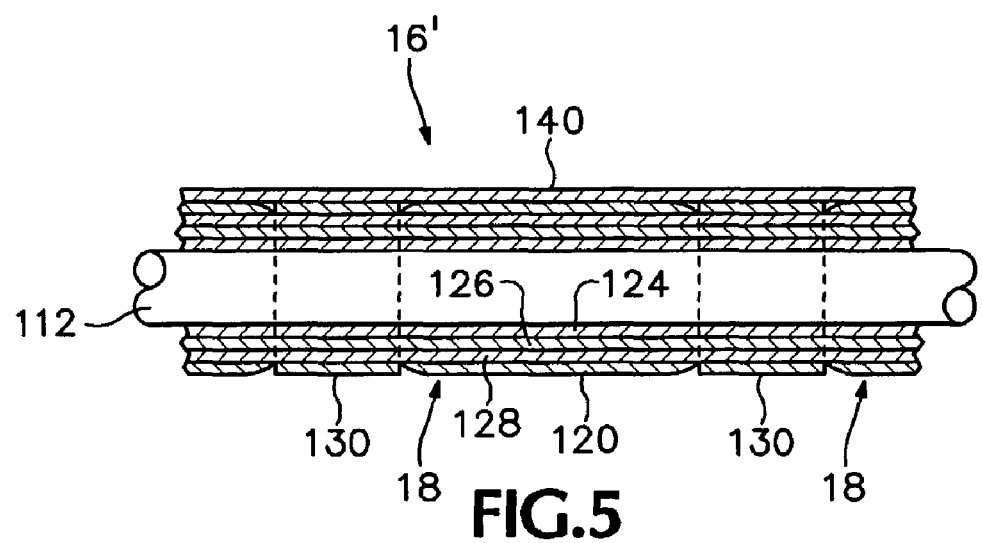
FIG. 5 is a greatly enlarged side view of an alternative embodiment of a sense wire that is part of the present invention.

Referring to FIGS. 1 and 2, in a first preferred embodiment, a blood analyte measurement assembly 10, according to the present invention includes a cartridge 12 housing a pay-out spool 14 and an uptake spool 15 of a membrane system coated wire assembly 16 bearing a number of sensing sites 18 (FIGS. 4 and 5). A set of guide rollers 17 maintain coated wire assembly 16 in proper tension as it is moved. A sensor positioning actuator 19 turns uptake spool 15, so that each sensing site 18 is in turn moved to be coincident with an aperture 20. In one preferred embodiment, sensor positioning assembly 19 includes an electric motor and a battery.

Referring to FIG. 4, in one preferred embodiment each sensing site 18 of assembly 16 is a location in which a layer of insulation 114 has been stripped off of a central conductor 112, which may be circular in cross section. Additionally, the central conductor 112 is coated with a membrane system that includes three membranes 124, 126 and 128 adapted to produce an electrical current, when exposed to an analyte bearing fluid, provided that a voltage is present on wire 112, relative to a nearby reference electrode (discussed further below).

One such membrane assembly is described in U.S. Pat. No. 5,165,407, issued Nov. 24, 1992. Another such membrane assembly is described in application Ser. No. 10/342,144 filed Jan. 13, 2003, which is assigned to the same assignee as the present application and is incorporated by reference as if fully set forth herein.

In one preferred embodiment membrane 124 is an interferent excluding layer made of a material such as sulphonated poly-ether sulphone or 3-amino phenol. Membrane 126 is made of an enzyme that reacts with glucose, such as glucose oxidase. Membrane 128 is a permselective layer for ensuring an adequate concentration of oxygen, relative to the concentration of glucose. Membrane 128 may be a copolymer of the type described in U.S. Pat. No. 5,428,123.

Referring to FIG. 5, in an alternative preferred embodiment, all of central conductor 112 of an alternative coated wire assembly 16' is coated with an analyte reactive membrane system 124, 126, and 128, which may be identical to layers 124, 126 and 128 in the system of FIG. 4 except for that the system of FIG. 5 is applied continuously by way of a sequence of three baths through which conductor 112 is drawn. Layer 128 is, in turn, coated with an absorbent layer 120, such as cellulose. Layer 120 controls the amount of blood that comes into contact with membrane layer 128 so that an exact known volume of blood is analyzed. Among other potential ranges, the volume of blood may be set at a level of between 50 nanoliters and 200 nanoliters of body fluid. A first sensing site 18 is separated from a second sensing site 18 by means of a constrictive band 130, which prevents the flow of blood between the two sites 18. A reference electrode is integrated into assembly 16' in the form of a grounded conductive strip 140 extending along one side of assembly 16'.

In an additional preferred embodiment, which may be illustrated by FIG. 4, a single layer of a mediated enzyme is used for the detection of glucose. In this case, referring to FIG. 4, layers 124, 126, and 128 are all the same and are composed of a mediated enzyme such as dimethyl ferrocene. The use of this mediated enzyme for detecting analytes is described in U.S. Pat. No. 4,545,382 and will be familiar to skilled persons. In this instance, however, this enzyme is applied directly to a conductive wire, circular in cross section, for directly sensing glucose.

For the embodiment of both FIG. 4 or FIG. 5, wire 112 may be a drawn filled tube of an electrochemically active metal, such as platinum, filled with a structurally robust material such as tantalum. In an alternative embodiment wire 112 is made of a structurally robust material, such as tantalum, plated or otherwise coated, by means such as vapor deposition, with an electrochemically active metal such as platinum. Other materials that may be used for the structurally robust material include stainless steel and nitinol (an alloy of titanium and nickel). In some embodiments the electroactive material may be gold. Wire 112 may have a diameter of between 10 and 300 microns.

One problem encountered in the type of technology discussed here is that of achieving a set, exactly repeated volume of enzyme in layer 126. One method for addressing this problem is to use an ink-jet nozzle to apply layer 126 onto the underlying surface.

Figures 3A, 3B:
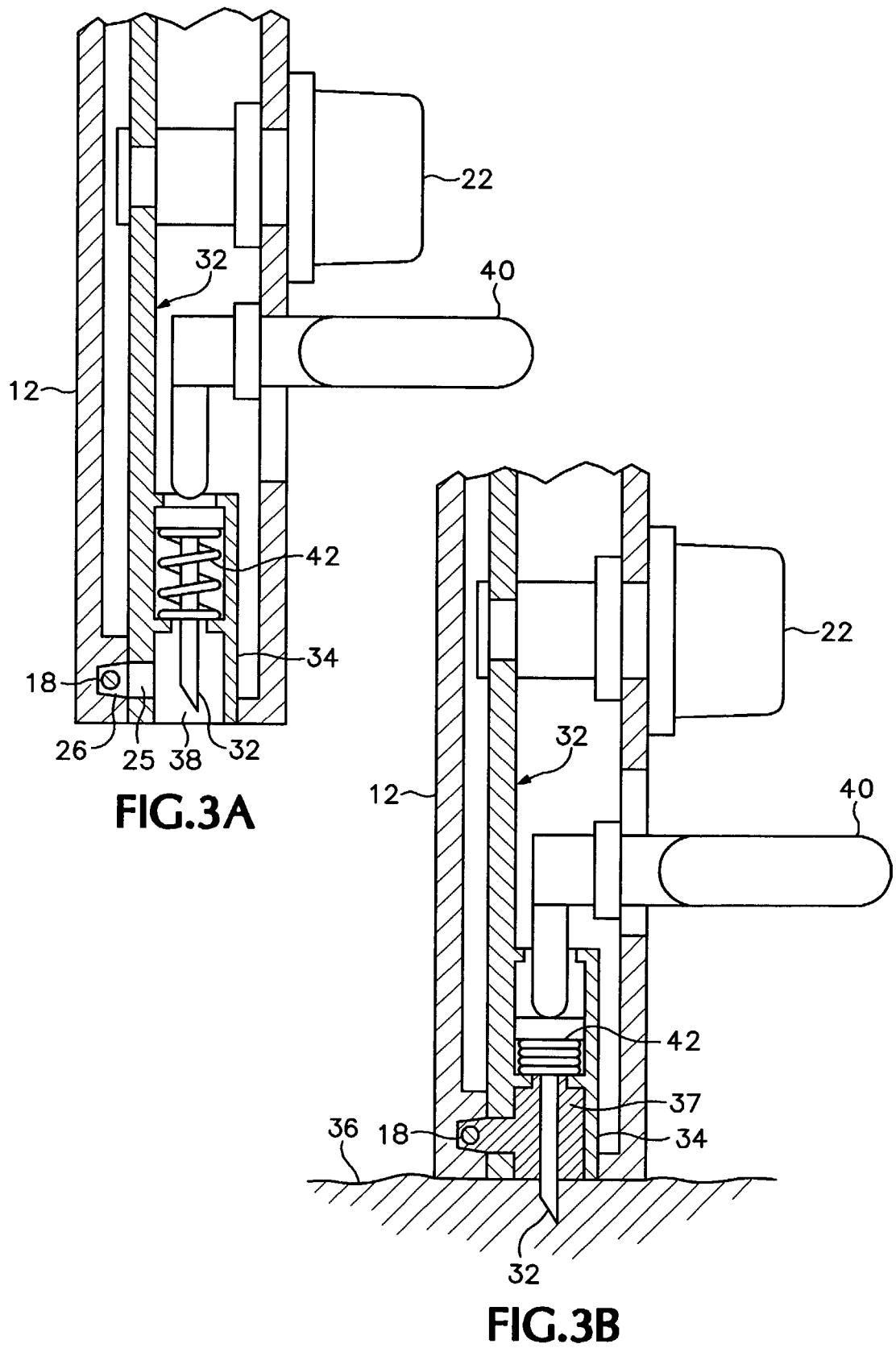
FIG. 3A is a detail section view of the cassette style multiple use analyte sensing assembly of FIG. 1.
FIG. 3B is a detail section view of the cassette style multiple use analyte sensing assembly of FIG. 1 showing the lancet in its protruding state.

Referring to FIGS. 2, 3A and 3B, together with spools 14 and 15, cartridge or housing 12 contains a multiple lancet holding mechanism 30 in the form of a wheel bearing a multiplicity of lancet assemblies 34 each containing a lancet 32 and defining a blood receiving cavity 38 (FIG. 3A). Each lancet assembly 34 includes an aperture 25 that cooperates with a notch 26 in housing 12, so that a sensing site 18 can be wetted with blood during test. A knob 22 is used to advance mechanism 30 before each blood glucose measurement so that a fresh lancet assembly 34 is positioned above aperture 20, coincident with a sensing site 18 on the coated wire 16.

To form a glucose measurement the user presses a button 28 (FIG. 1) on housing 12 causing the sensor positioning actuator 19 to move a fresh measurement site into alignment with the housing aperture 20 (FIG. 2). The user also turns a knob 22 to move a fresh lancet assembly to be coincident with aperture 20. The cartridge 12 is pressed against the skin 36 at aperture 20 and a manual actuator 40 is used by the patient to press lancet 34 through skin 36, causing blood 37 to flow into cavity 38. A voltage application and current sensing block 21 (FIG. 1) places a voltage onto conductor 112 (FIG. 4) and the flow of current through conductor 112 is measured, indicating the glucose level in the blood 37. In the embodiment of FIG. 5 strip 140 is the reference electrode. Otherwise lancet 32 or skin 36 serves as a reference. After cavity 38 is sufficiently filled with blood 37, the patient may pull upwardly on actuator 40, thereby permitting spring 42 to pull lancet 34 back into assembly 32.

After block 21 completes sensing of the current flowing through central conductor 112, sensing site 18 is moved away from aperture 20 by action of actuator 19. In one preferred embodiment aperture 20 is closed between sensing operations by a sliding closure 50, to prevent contamination of media 16.

Skilled persons will readily appreciate the many advantages of the above described assembly 10. In many respects this assembly 10 bears the relationship to currently available glucose testing system as a cartridge film camera, or disposable camera, bears to the type of camera in which the film had to be loaded frame by frame. The patient simply presses a button, pushes in the lancet and waits a short while for the result. The step of disposing of a paper strip has been eliminated. Because the tubular housing receives a volume of blood that is on the order of a micro liter, which quickly dries, there appears to be no problem of blood disposal. Moreover, because the step of producing individual sensing elements has been eliminated, it appears that the cost of each sensing site can be reduced to a fraction of a penny.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A multiple use analyte sensing assembly, comprising:
   (a) a long, thin electrical conductor;
   (b) a plurality of sensing sites spaced along said electrical conductor, each said sensing site including a membrane system adapted to create a current in conjunction with said electrical conductor when each said sensing site is placed into contact with body fluid containing an analyte;
   (c) a housing, having a housing aperture;
   (d) an uptake spool and a payout spool, located within said housing, said electrical conductor being wrapped about said payout spool and threaded to said uptake spool prior to said sensing assembly being used;
   (e) a sensor positioning actuator for turning said uptake spool so that each said sensing site is moved, in sequence, to said housing aperture and to said uptake spool; and (f) a skin broaching assembly, having:
  (i) a multiple lancet holding mechanism;
  (ii) a multiplicity of lancets held by said multiple lancet holding mechanism;
  (iii) a lancet positioning actuator adapted to move, in sequence, each lancet to a position coincident to said housing aperture; and
  (iv) a lancet use actuator adapted to move a lancet that is positioned coincident to said housing aperture, at least partially through said housing aperture and then back again.

2. The multiple use analyte sensing assembly of claim 1, wherein said membrane system is a single membrane system that is continuous along said electrical conductor.

3. The multiple use analyte sensing assembly of claim 1, wherein said electrical conductor is covered with insulation, and wherein said insulation is absent in a plurality of regions, said plurality of regions being the locations of said sensing sites where said membrane system has been applied.

4. The multiple use analyte sensing assembly of claim 1, wherein said membrane system is covered by an absorbent layer.

5. The multiple use analyte sensing assembly of claim 4, wherein tight bands are interspersed about said absorbent layer between sensing sites to prevent blood entering a first sensing site of said plurality of sensing sites from a second sensing site of said plurality of sensing sites.

6. A method of taking a sequence of blood analyte measurements, comprising:
  (a) providing an analyte sensing assembly, including:
    (i) a lengthwise electrical conductor; and
    (ii) a first measurement site and a second measurement site located along said lengthwise electrical conductor, each said measurement site including a membrane assembly adapted to create an electrical current flowing out of said lengthwise electrical conductor in the presence of an analyte when a voltage is placed on said lengthwise electrical conductor relative to ground;
  (b) forming a first analyte measurement by placing a voltage on said lengthwise electrical conductor, exposing said first measurement site to body fluid, and measuring electrical current in said lengthwise electrical conductor; and
  (c) subsequent to forming said first analyte measurement, forming a second analyte measurement by placing a voltage on said lengthwise electrical conductor, exposing said second measurement site to body fluid and measuring electrical current in said lengthwise electrical conductor.

7. The method of claim 6, wherein said analyte sensing assembly includes further measurement sites, in addition to said first measurement site and said second measurement site.

8. The method of claim 6, wherein said analyte sensing assembly includes a reference electrode for each measurement site.

9. The method of claim 6 wherein said body fluid comes from a patient having skin, and wherein said body fluid rests on said skin during forming of said first analyte measurement and said second analyte measurement and wherein said skin of said patient serves as a reference electrode.

10. The method of claim 6 wherein said membrane assembly includes more than one type of membrane.

11. The method of claim 6 wherein said first measurement site is positionally associated with a body fluid retention element at the time said first measurement is formed and said second measurement site is positionally associated with said body fluid retention element at the time said second measurement is formed.

12. The method of claim 11 wherein said body fluid retention element is a cavity traversed by said first and second measurement sites.

13. The method of claim 11 wherein said body fluid retention element comprises absorbent material.

14. The method of claim 6 wherein said lengthwise electrical conductor is a wire.

15. The method of claim 6 wherein said membrane assembly is present only at said measurement sites.

16. The method of claim 6 wherein said lengthwise electrical conductor is coated by said membrane assembly at said measurement sites as well as between said measurement sites.

17. An analyte sensing assembly, including:
  (a) a lengthwise electrical conductor having an outer surface; and
  (b) a first measurement site and a second measurement site located along the outer surface of said lengthwise electrical conductor, each said measurement site including a membrane assembly adapted to create, in the presence of an analyte, an electrical current flowing out of said lengthwise electrical conductor when a voltage has been placed on said lengthwise electrical conductor relative to ground.

18. The assembly of claim 17, wherein said analyte sensing assembly includes further measurement sites, in addition to said first measurement site and said second measurement site.

19. The assembly of claim 17, wherein said analyte sensing assembly includes a reference electrode for each measurement site.

20. The assembly of claim 17 wherein said membrane assembly includes more than one membrane.

21. The assembly of claim 17 wherein said first measurement site is positionally associated with a body fluid retention element at the time said first measurement is formed and said second measurement site is positionally associated with said body fluid retention element at the time said second measurement is formed.

22. The assembly of claim 21 wherein said body fluid retention element is a cavity traversed by said first and second measurement sites.

23. The assembly of claim 21 wherein said body fluid retention element comprises absorbent material.

24. The assembly of claim 17 wherein said lengthwise electrical conductor is a wire.

25. The assembly of claim 17 wherein said membrane assembly only exists at said measurement sites.

26. The assembly of claim 17 wherein said lengthwise electrical conductor is coated by said membrane assembly at said measurement sites and between said measurement sites.

27. The multiple use analyte sensing assembly of claim 1, wherein said membrane system comprises an interferent excluding membrane, an enzyme membrane, and a permselective membrane.

28. The method of claim 6, wherein said membrane assembly comprises an interferent excluding membrane, an enzyme membrane, and a permselective membrane.

29. The assembly of claim 17, wherein said membrane assembly comprises an interferent excluding membrane, an enzyme membrane, and a permselective membrane.

30. The assembly of claim 17, wherein said lengthwise electrical conductor is circular in cross-section.

31. The assembly of claim 17, wherein said first measurement site and said second measurement site are separated from each other by insulation.

32. The assembly of claim 17, wherein said first measurement site and said second measurement site are separated from each other by a constrictive band.

33. The assembly of claim 17, wherein said first and second measurement sites encircle the lengthwise electrical conductor.

* * * * *